United States Patent
Huang et al.

(10) Patent No.: US 10,323,851 B2
(45) Date of Patent: Jun. 18, 2019

(54) UV TUBE FOR KILLING MICROORGANISMS AND AIR CONDITIONING SYSTEM COMPRISING THE TUBE

(71) Applicant: Sentec E&E Co., Ltd., Taoyuan (TW)

(72) Inventors: Jason An-Cheng Huang, Taoyuan (TW); Tzu-Chi Cheng, Taoyuan (TW)

(73) Assignee: Sentec E&E Co., Ltd., Taoyuan (TW)

( * ) Notice: Subject to any disclaimer, the term of this patent is extended or adjusted under 35 U.S.C. 154(b) by 0 days.

(21) Appl. No.: 15/853,484

(22) Filed: Dec. 22, 2017

(65) Prior Publication Data
US 2019/0049129 A1    Feb. 14, 2019

(30) Foreign Application Priority Data
Aug. 11, 2017  (TW) .............................. 106127323 A

(51) Int. Cl.
*A61L 9/20* (2006.01)
*C02F 1/32* (2006.01)
*F24F 3/16* (2006.01)

(52) U.S. Cl.
CPC .................................... *F24F 3/16* (2013.01); *A61L 9/20* (2013.01); *C02F 1/32* (2013.01); *A61L 2209/111* (2013.01); *A61L 2209/12* (2013.01); *C02F 2201/326* (2013.01); *C02F 2201/3228* (2013.01); *F24F 2003/1667* (2013.01)

(58) Field of Classification Search
CPC ......... F24F 3/16; A61L 9/20; A61L 2209/111; C02F 1/32; C02F 2201/3228; C02F 2201/326
See application file for complete search history.

(56) References Cited

U.S. PATENT DOCUMENTS

| | | | | | |
|---|---|---|---|---|---|
| 3,105,733 | A | * | 10/1963 | Gennady | A61L 9/20 422/121 |
| 4,255,663 | A | * | 3/1981 | Lewis | A61L 2/10 250/436 |
| 5,382,805 | A | * | 1/1995 | Fannon | H01K 1/325 250/424 |
| 5,835,840 | A | * | 11/1998 | Goswami | A61L 9/20 422/186.3 |
| 6,471,136 | B1 | * | 10/2002 | Chatterjee | F25D 17/042 237/2 B |
| 6,500,387 | B1 | * | 12/2002 | Bigelow | A61L 9/20 250/432 R |

(Continued)

*Primary Examiner* — Kun Kai Ma
(74) *Attorney, Agent, or Firm* — Wang Law Firm, Inc.

(57) ABSTRACT

A UV tube for killing microorganisms in a fluid generally includes a hollow tubular body, a UV isolation layer, and at least one UV light source. The hollow tubular body has an inlet port, an outlet port, and a fluid channel portion between the inlet port and the outlet port. The fluid channel portion has an inner surface. The UV isolation layer is disposed at the inner surface of the hollow tubular body for sheltering the inner surface of the hollow tubular body. The fluid is allowed to flow through the UV isolation layer. The UV light source is provided at the hollow tubular body and/or the UV isolation layer. The UV isolation layer can absorb and/or reflect the ultraviolet light emitting from the UV light source, so that the possibility of the fluid channel portion being irradiated by the UV light can be reduced.

8 Claims, 7 Drawing Sheets

(56) References Cited

U.S. PATENT DOCUMENTS

| | | | | |
|---|---|---|---|---|
| 6,614,028 B1* | 9/2003 | Cekic | A61L 2/0011 250/432 R |
| 6,773,608 B1* | 8/2004 | Hallett | A61L 2/0047 210/748.11 |
| 7,514,696 B2* | 4/2009 | Spector | A61N 5/0616 250/435 |
| 7,625,277 B2* | 12/2009 | Palmer | A61L 9/20 454/255 |
| 8,168,122 B2* | 5/2012 | Lee | A61L 2/208 422/120 |
| 8,585,980 B2* | 11/2013 | Tupman | A61L 9/205 422/122 |
| 9,370,600 B1* | 6/2016 | DuPuis | A61L 9/20 |
| 9,808,544 B2* | 11/2017 | Cooper | B01J 19/123 |
| 9,834,456 B2* | 12/2017 | Collins | C02F 1/325 |
| 2003/0062526 A1* | 4/2003 | Romano | B82Y 20/00 257/79 |
| 2005/0062412 A1* | 3/2005 | Taniguchi | H01L 51/0096 313/512 |
| 2005/0115498 A1* | 6/2005 | Ingram | F26B 3/28 118/642 |
| 2009/0217690 A1* | 9/2009 | Silderhuis | A61L 9/205 62/264 |
| 2010/0028201 A1* | 2/2010 | Neister | A61L 2/0011 422/24 |
| 2012/0093684 A1* | 4/2012 | Martin | H05B 41/2325 422/4 |
| 2012/0171079 A1* | 7/2012 | Morito | A61L 2/088 422/121 |
| 2013/0153514 A1* | 6/2013 | Stern | C02F 1/325 210/748.1 |
| 2015/0064069 A1* | 3/2015 | Yi | A61L 9/20 422/121 |
| 2015/0246148 A1* | 9/2015 | Blechschmidt | A61L 2/10 422/4 |
| 2015/0306269 A1* | 10/2015 | Bullard | A61L 9/14 422/4 |
| 2017/0028820 A1* | 2/2017 | Walsh | A61L 9/20 |
| 2017/0252066 A1* | 9/2017 | Worrilow | C12N 5/0604 |

* cited by examiner

UV TUBE FOR KILLING MICROORGANISMS AND AIR CONDITIONING SYSTEM COMPRISING THE TUBE

FIELD OF THE INVENTION

The present invention relates to a UV tube and an air conditioning system comprising the tube.

BACKGROUND OF THE INVENTION

To become healthy, in addition to regular exercise, nutritional supplements, and a proper rest, a person should prevent the invasions of external pathogens, such as bacteria or viruses. Killing bacteria and viruses has been applied for a long time to reduce infection. There are many methods to remove microorganisms, including bacteria, viruses and other pathogens. The methods include killing microorganisms directly to reduce their threats to human health, and filtering microorganisms to excluding them from the scope of human life.

Due to the fact that life automatically seeks substainable reproduction, pathogens evolve as the environment updates. Pathogens must rely on water, air or other media to survive and spread. To face the potential threats of pathogens, several methods of killing microorganisms are developed, which are mainly divided into physical methods and chemical methods. The physical methods include filtering and heating. As an example, the heating method can use steam to heat an object to allow the temperature of the object's surface to reach 100 degrees or more. The chemical method can employ bactericides, such as ozone or bleach, to kill microorganisms. However, each method has its limitation and cannot be applied to all cases for killing pathogens. Some methods are difficult to be implemented because of inconvenient operation.

Currently, some manufacturers are dedicated to improve filters used in air conditioning systems, one of which is granted U.S. Pat. No. 9,518,487, wherein a filtering element is provided with a photocatalyst 7 (see FIG. 1), which has good activity. The photocatalyst is irradiated by ultraviolet light so that, when pathogens (such as bacteria or viruses) are carried by an air flow to pass through the filter, the pathogens may react with the photocatalyst. Therefore, the pathogens can be decomposed, and thus the air can be purified. The photocatalyst can be titanium dioxide, activated carbon, or nano silver. The titanium dioxide requires irradiation of ultraviolet light. One example of activated carbon is disclosed in U.S. Pat. No. 8,172,925.

However, the performance of a catalyst depends on whether pathogens are in contact therewith or not. When pathogens contact catalyst, decomposition reaction thereof can be initiated. If the pores of a filter are too large, the pathogens in the air may pass through the pores, without contacting the catalyst on the filter, so that the pathogens can reach a human body and cause a threat to the human body. On the other hand, if the pores of the filter are too small, although the possibility of pathogens contacting the catalyst can be increased, dust or decomposed pathogens are easy to remain on the filter, causing the filter to be blocked. Consequently, the air passing through the filter is quickly reduced. Currently, for increasing the possibility of pathogens contacting a catalyst, a multi-layered filter has been developed. However, this may lead to a large filter, which usually has a higher cost. Particularly, when UVA radiation (wavelength about 315-400 nm) or UVB radiation (wavelength about 280-315 nm) is employed, due to poor penetration of this radiation, the performance of the multi-layered filter can be reduced significantly.

As to UVC radiation (wavelength about 100-280 nm), which has a shorter wavelength and a higher frequency than the previous two types of UV radiation, due to higher energy of each photon, not only does the UVC radiation kill pathogens, also enables the material or electronic components exposed thereunder to age rapidly, thus resulting in photodegradation. In natural world, due to atmospheric protection, the UVC in space cannot reach the surface of the earth. As commonly known, UVC radiation may cause harm to the human body because of its high energy. For UVC radiation, since safety issues associated therewith should be considered more carefully, application of UVC radiation is limited. Another problem in using ultraviolet light is light attenuation, which is resulted from dissipation during transmission. The lost energy during transmission of ultraviolet light cannot be used on sterilization.

Accordingly, it is expected that today's sterilization method can effectively and completely eliminate the threats caused by pathogens, and the method will not cause damages to other objects. In addition to an effective process, the sterilization method should guarantee the safety of human beings and other associated members, and this is one goal that the present invention seeks to achieve.

SUMMARY OF THE INVENTION

One object of the present invention is to provide a UV tube, which employs a hollow tubular body furnished with a UV isolation layer and a UV light source for effectively and completely killing microorganisms contained in a fluid that flows through the UV tube.

Another object of the present invention is to provide a UV tube furnished with a UV isolation layer and a UV light source, which can prevent the ultraviolet light emitting from the UV light source from leaking out and causing damages to the tubular body or causing risk to a user.

A further object of the present invention is to provide a UV tube furnished with a UV isolation layer and a UV light source, which is simply in structure and can reduce the manufacturing cost.

A still further object of the present invention is to provide an air conditioning system, which employs a UV light source in cooperation with a UV tube provided with a UV isolation layer for directly and effectively killing microorganisms contained in an air flow so as to clean the air.

A yet still further object of the present invention is to provide an air conditioning system, which includes a UV tube and is simple in structure and can reduce the manufacturing cost.

The UV tube, which can be connected with a fluid drive means, comprises a hollow tubular body, a UV isolation layer, and at least one UV light source. The hollow tubular body has an inlet port, an outlet port, and a fluid channel portion between the inlet port and the outlet port, wherein the inlet port takes in a fluid delivered by the fluid drive means, while the outlet port allows the fluid to flow out of the hollow tubular body, and the fluid channel portion has an inner surface. The UV isolation layer is disposed at the inner surface of the hollow tubular body for sheltering the inner surface of the hollow tubular body. The fluid is allowed to flow through the UV isolation layer. The UV light source is provided at the hollow tubular body and/or the UV isolation layer. The UV light source can emit ultraviolet light which has a wave length between 100 and 280 nm and reaches a light intensity level more than 40 micro-watt/square-centimeter in at least one portion of a space defined by the inner surface. The UV isolation layer can absorb and/or reflect at least 80% of the ultraviolet light emitting from the UV light source, so that the possibility of the fluid channel portion being irradiated by the UV light can be reduced As a summary, the UV tube of the present invention employs a hollow tubular body cooperated with a UV light source to simplify the structure of the UV tube and reduce the manufacturing cost. The ultraviolet light emitting from the UV light source can directly and completely kill microorganisms contained in a fluid to increase the sterilization effect. Particularly, the hollow tubular body is furnished with a UV isolation layer, so that damages caused by leakage of the ultraviolet light can be reduced. In addition, the UV tube can be cooperated with a biosensor, which can accurately control the speed of the fluid flowing through the UV tube to increase the efficiency of killing microorganisms.

BRIEF DESCRIPTION OF THE DRAWINGS

The foregoing and other features and advantages of illustrated embodiments of the present invention will be more readily apparent from the following detailed description, which proceeds with reference to the accompanying drawings.

DETAILED DESCRIPTION OF THE ILLUSTRATED EMBODIMENTS

The foregoing and other technical contents, features and advantages of the present invention will be illustrated in detail by way of exemplary embodiments with reference to the accompanying drawings. In the exemplary embodiments, same elements will be indicated by similar numerals or labels.

Figure 1:
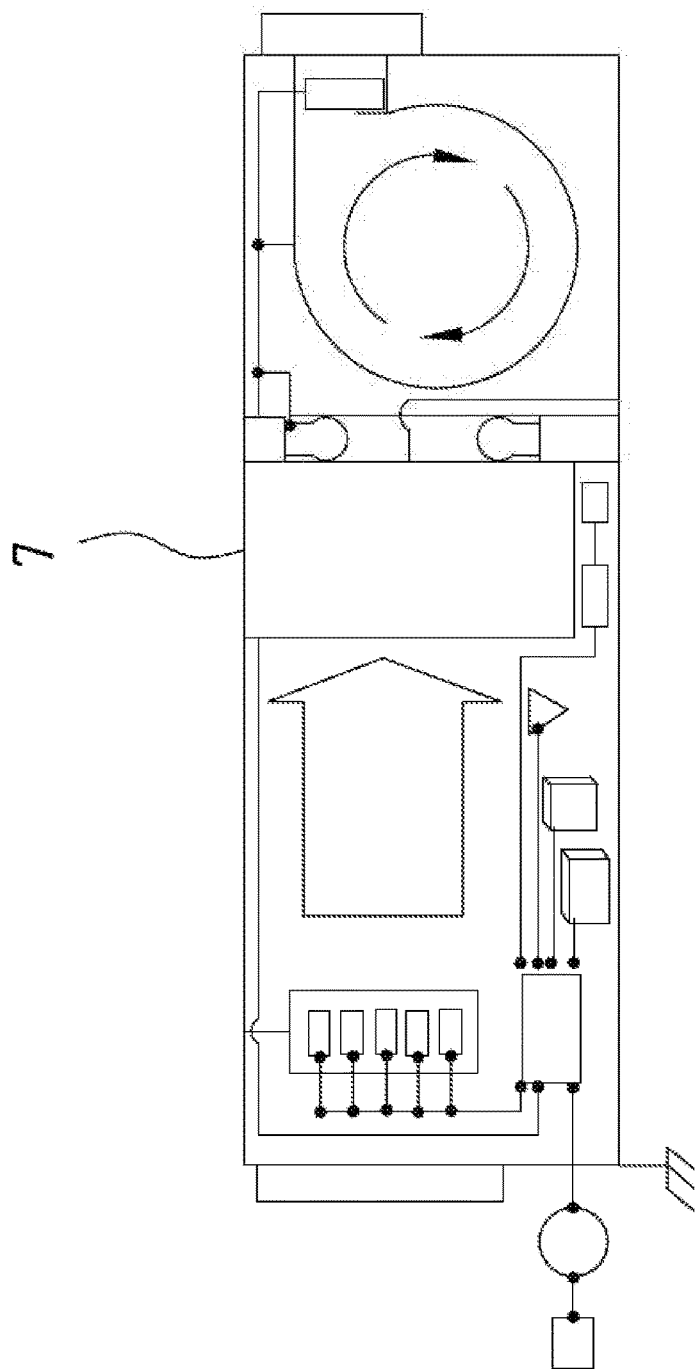
FIG. 1 shows a schematic view of an air conditioning system of a prior art, wherein a photocatalyst is employed.
Figure 2:
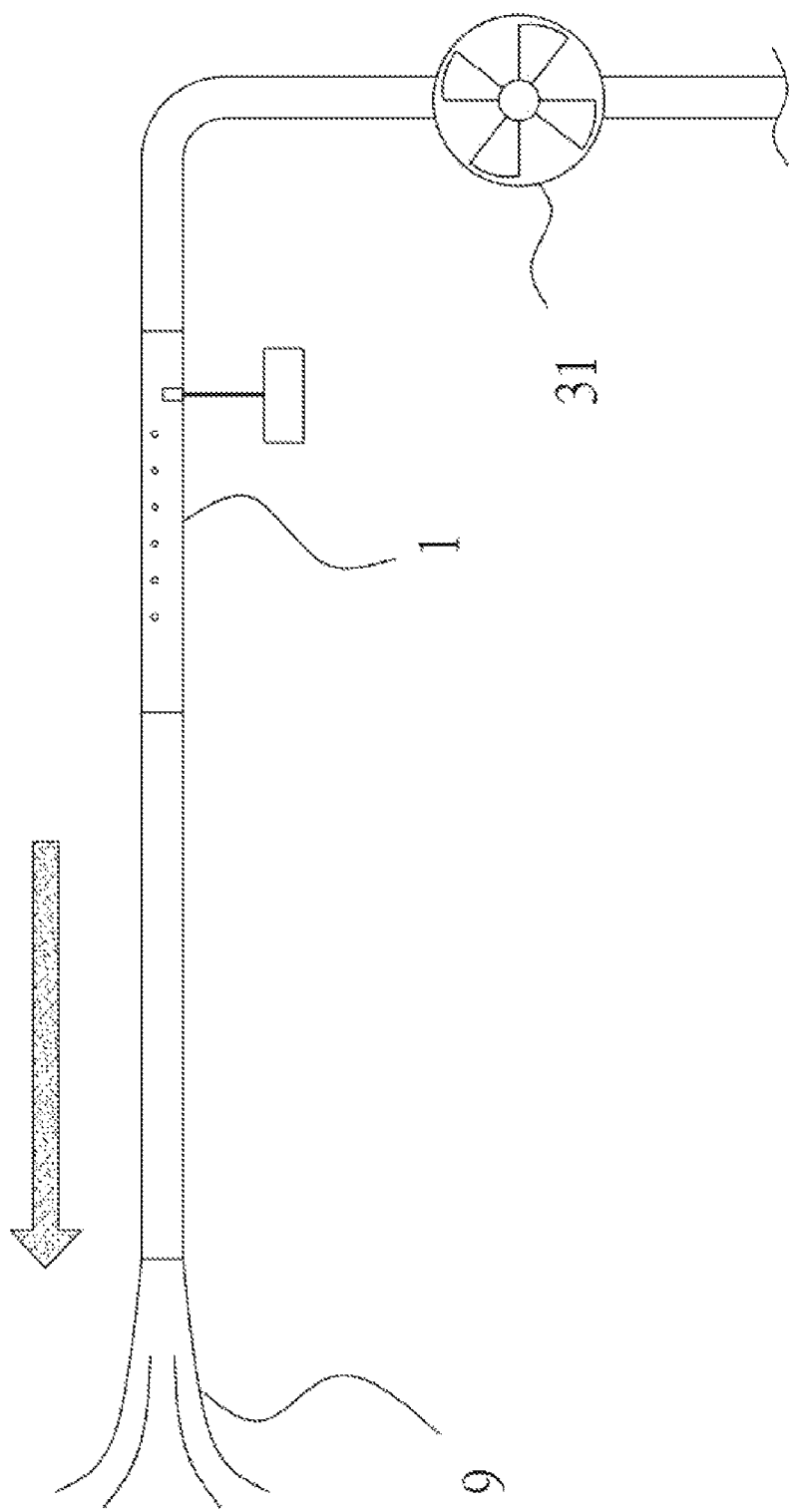
FIG. 2 shows a schematic view of a first embodiment of the present invention, wherein a UV tube is connected with a fluid drive means that delivers an air flow.

Referring to FIG. 2, a UV (ultraviolet) tube 1 for killing microorganisms according to a first embodiment is shown, which can be installed in a vehicle air conditioning system. As shown, the UV tube 1 is in connection with a fan device, which works as a fluid drive means 31, so that the air from the inside and/or outside of the vehicle, indicated as a fluid 9, can be taken in. The vehicle is not limited to a bus or truck. Of course, the air conditioning system can be adapted to be a household air conditioning system without affecting the essence of the present invention.

Figure 3:
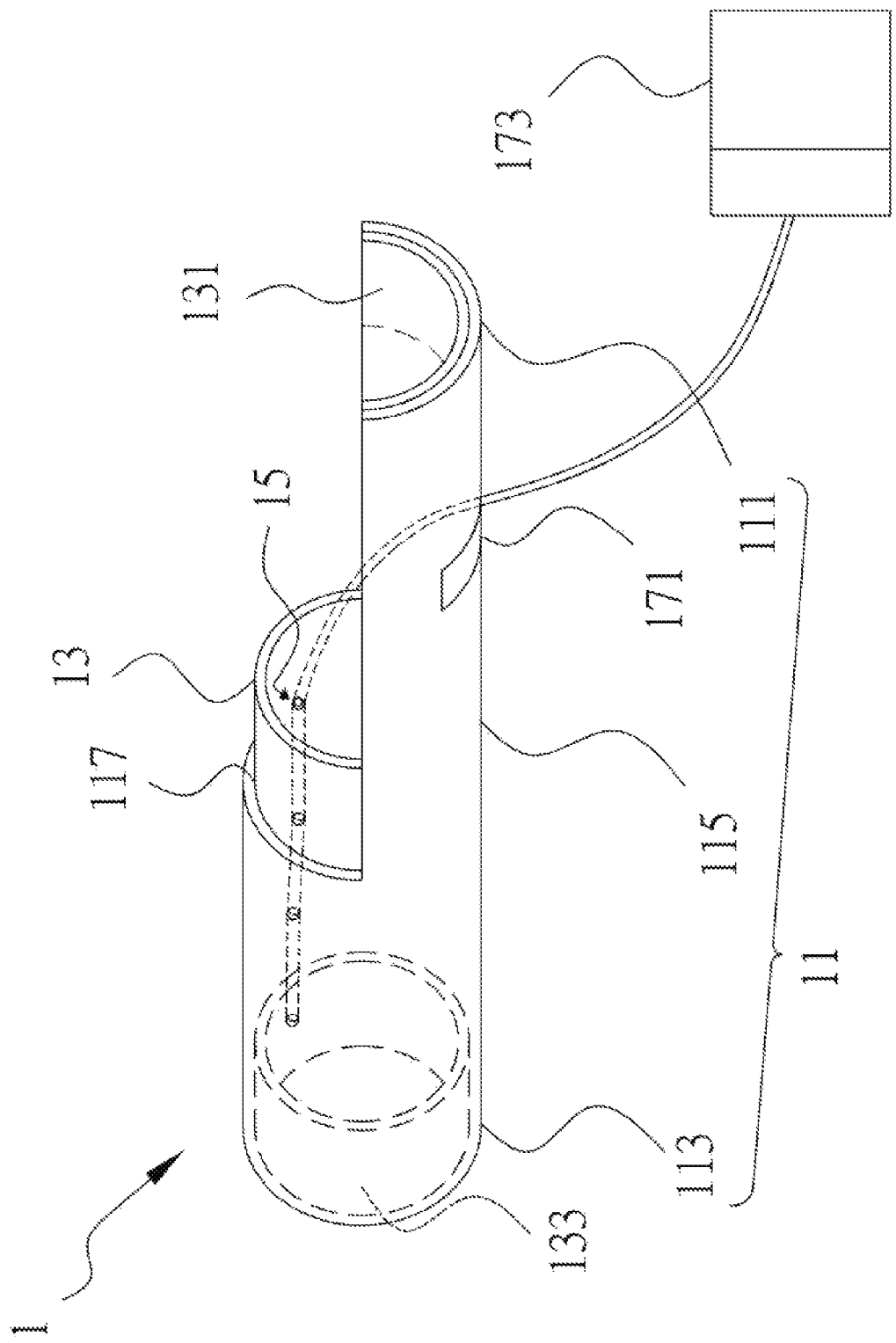
FIG. 3 shows a partially sectional view of the first embodiment, which shows an internal structure of the UV tube.

Referring to FIG. 3 in conjunction with FIG. 2, the UV tube 1 is provided with a UV isolation layer 13, which can be an extruded aluminum tube. Of course, those skilled in the art understands that the UV isolation layer 13 can be made by tin or other materials suited for being extruded; or alternatively, the UV isolation layer 13 can be a cast or drawn hollow metal tube of copper or other materials; or alterantively, the UV isolation layer 13 can be made by adding a material capable of absorbing or reflecting ultraviolet light to a metal. In this application, a hollow metal tube made of a ductile metal material, such as aluminum or copper, is defined as a ductile metal layer.

The UV isolation layer 13, made of a ductile metal, can be placed in a plastic injection mold. By using insert molding technique, a hollow tubular body 11 can be formed at the outer surface of the ductil metal layer. For easy of illustration, the end portion of the hollow tubular body for connecting with an upstream air tube is termed as an inlet port 111, while the opposite portion of the hollow tubular body 11, through which the air flows out of the tube, is termed as an outlet port 113. The portion of the hollow tubular body 11 located between the inlet port 111 and the outlet port 113 is termed as a flow channel portion 115. Therefore, the UV isolation layer 13 can be tightly located at an inner surface 117 of the flow channel portion 115. Of course, the UV isolation layer 13 and the outer hollow tubular body 11 can be made of two different metals or alloys, or a metallic material and a ceramic material respectively, without departing from the essence of the present invention.

UVC LED dies, each with a light intensity level of 2250 micro-watt/square-centimeter, can be used as the UV light source 15. Each LED die when enabled can emit ultraviolet light having a wavelength about 254 nm (UVC). Each LED die can be soldered onto a soft circuit board and located at an inner surface of the UV isolation layer 13. In this embodiment, for killing bacilli, which has a greater ability to resist ultraviolet light, the air within the tube is expected to receive UV irradiation from the UV light source 15 to at least reach a cumulative light intensity level of 22000 micro-watt sec/square-centimeter. To accomplish this purpose, this embodiment employs 12 UVC LED dies.

Furthermore, the UV tube 1 can be provided with a biosensor 171. As an example, the biosensor can be a piece of laser photography equipment employing laser as flash for taking a high resolution, low noise image, which can be enlarged so that analysis can be made analysis to check whether there are surviving pathogens contained in the fluid 9 and even to track the movement state of the pathogens contained in the fluid 9. The biosensor can convert the information of organisms contained in the fluid into a feedback signal sent back to the processor 173, so that the electrical current supplied to the UV light source 15 can be increased to adjust the ultraviolet light intensity; or the delivering pressure of the fluid drive means 31 can be reduced to adjust the velocity of the fluid 9, so that the time of the fluid 9 being exposed to the ultraviolet light can be increased, and thus the fluid 9 can receive more UV irradiation to reach a higher level of culmulative light intensity, thus increasing the bactericidal effect.

Furthermore, the UV isolation layer 13 can be integrally formed with a first intermediary section 131 adjacent to the inlet port 111, and a second intermediary section 133 adjacent to the outlet port 113. When the UV light source 15 is enabled, the UV isolation layer 13 made of aluminum can absorb and reflect the ultraviolet light emitting from the UV light source 15. The UV isolation layer 13 can reduce leakage of the ultraviolet light to prevent a significant reduction in light intensity, so that the bactericidal effect within the irradiation range of the UV light source can be guaranteed. Moreover, the first intermediary section 131 and the second intermediary section 133 may further increase the time of the air being exposed to the ultraviolet light within the tube, and can prevent a large amount of the ultraviolet light from entering the hollow tubular body 11, thus avoiding photodegradation of the hollow tubular body 11 in a short time.

Figure 4:
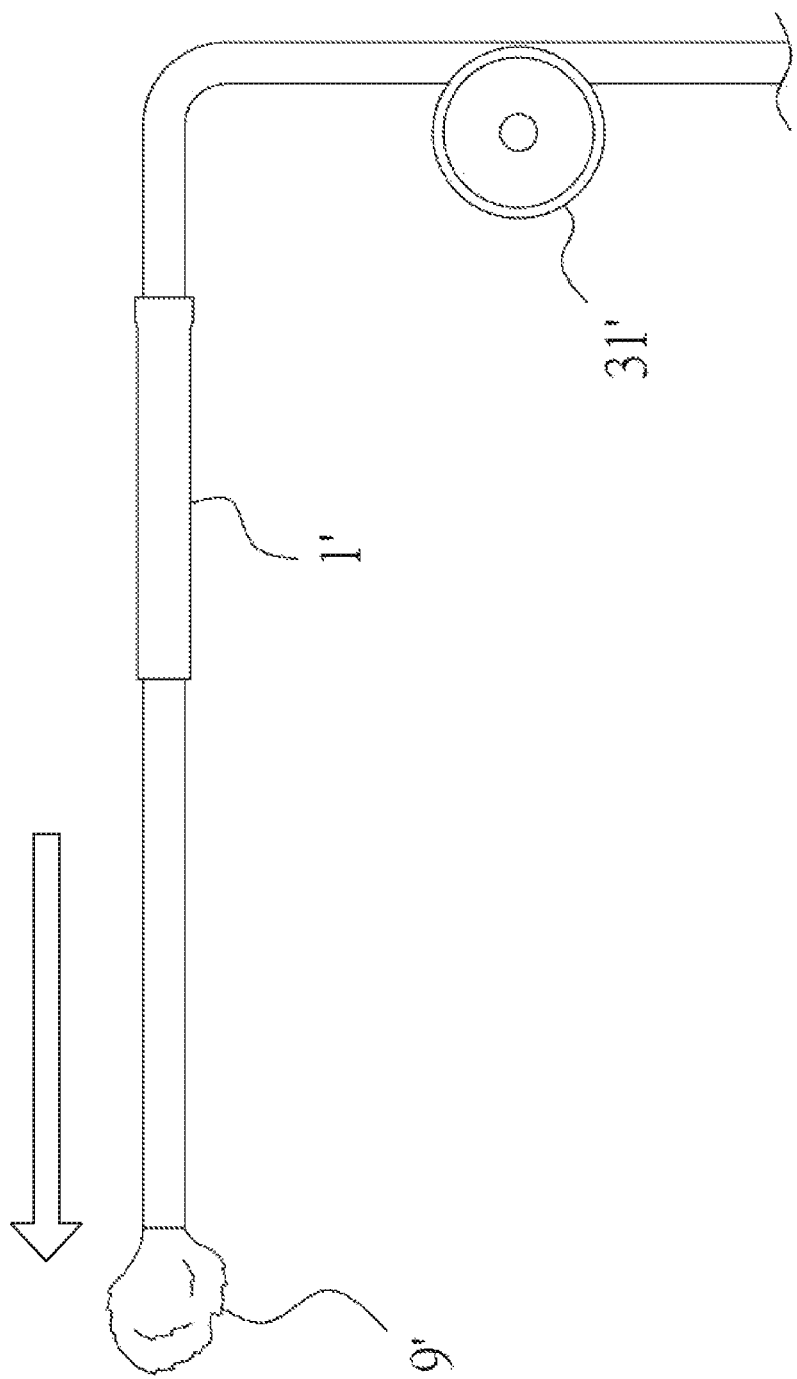
FIG. 4 shows a schematic view of a second embodiment of the present invention, wherein a UV tube is connected with a fluid drive means that delivers a water flow.

FIG. 4 shows a second embodiment of the present invention, which is concerned with a UV tube 1' used in a generally household water treatment system for killing microorganism contained in water and, particularly suitable for being connected to a tap water pipe to provide a procedure for killing microorganisms contained in tape water. In this embodiment, the fluid 9' refers to a flow of tap water, and the fluid drive means 31' refers to a household pump, wherein a flow of tap water can be pumped to pass through the UV tube 1' and then supplied to each tap water faucet. The tap water can be used only after passing through the UV tube 1' where pathogens contained in the tap water can be killed.

Figure 5:
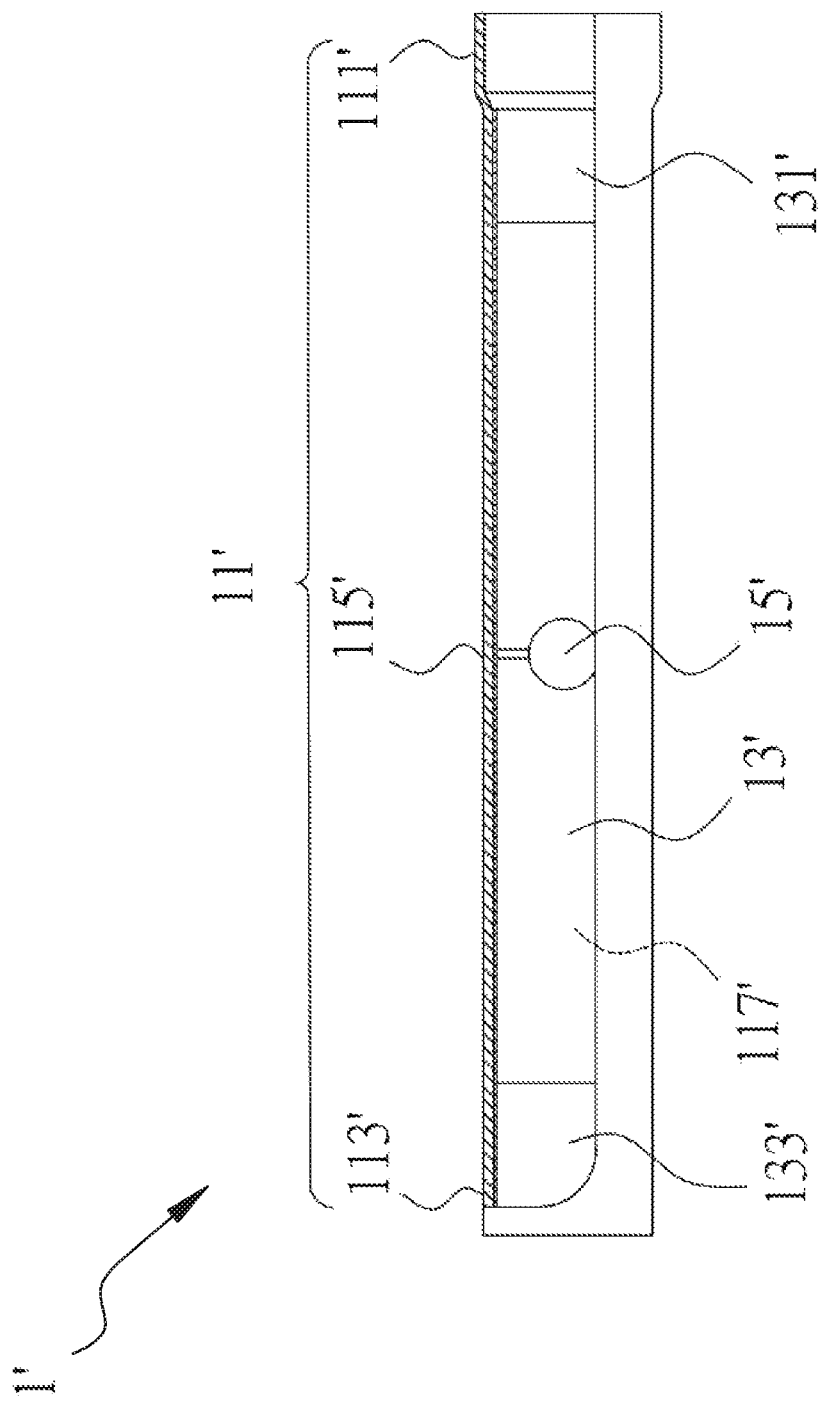
FIG. 5 shows a partially sectional view of the second embodiment, which shows an internal structure of the UV tube.
Figure 6:
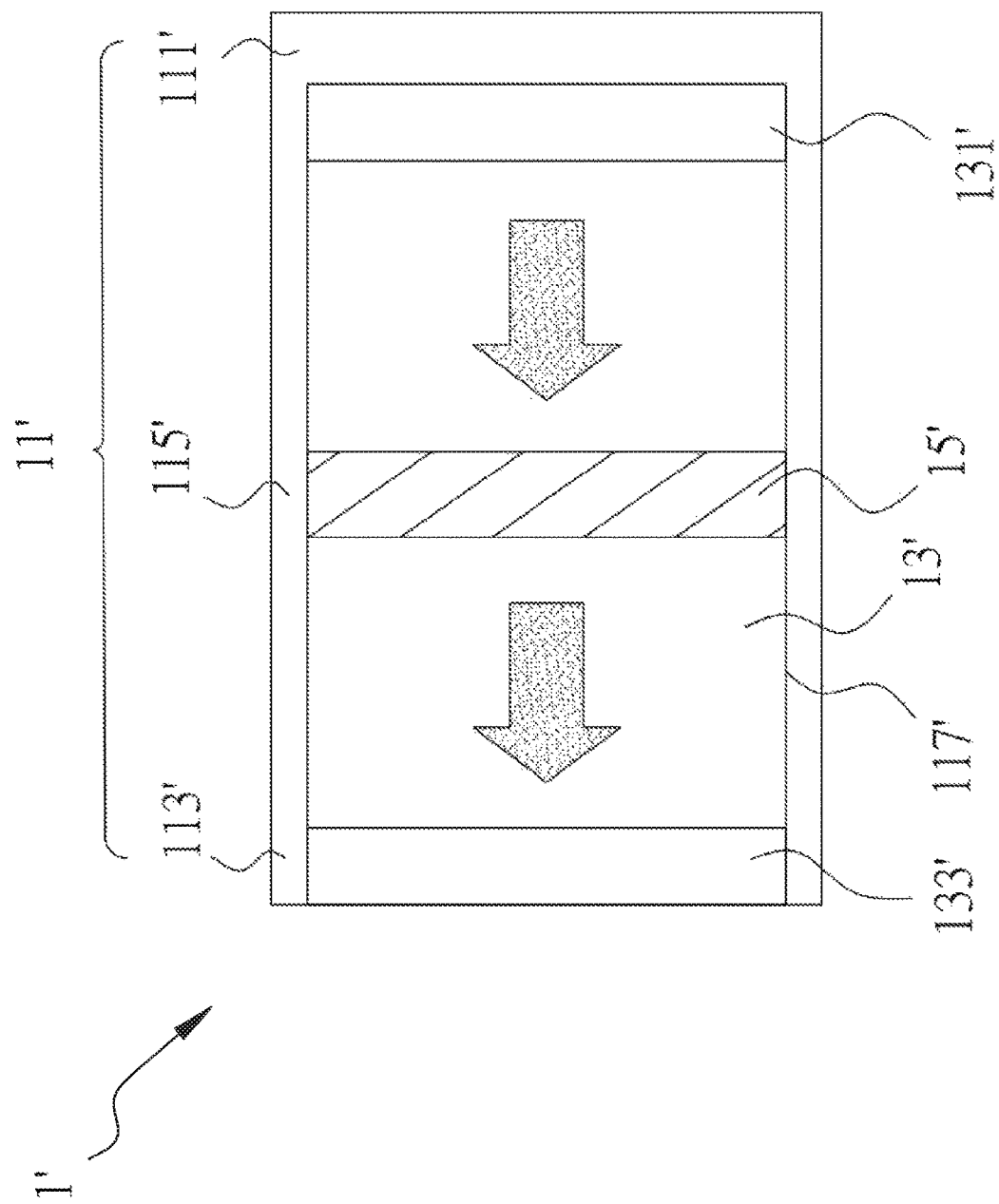
FIG. 6 shows a schemtic view of the second embodiment, which shows an internal structure and the flow direction of a fluid.

FIGS. 5 and 6 show a hollow tubular body 11'. As an example, it can be a polypropylene product. The hollow tubular body 11' is formed with an inlet port 111' for taking in water, an outlet port 113' for allowing the water to flow out of the hollow tubular body 11', and a flow channel portion 115' between the inlet port 111' and the outlet port 113'. The inlet port 111' has a diameter slightly larger than the other portions of the hollow tubular body 11'. The flow channel portion 115' has an inner surface 117', which can be electroplated with a metal layer to form a UV isolation layer 13' which shelters the inner surface 117' so as to protect the hollow tubular body 11'. In this embodiment, the UV isolation layer 13' can be a copper layer; however, other harmless metals can also be used for making the UV isolation layer 13'.

The hollow tubular body 11' is provided therein with a UV light source 15'. As an example, the UV light source 15' is implemented by two UV high pressure mercury lamps, which are hermetically fixed in the hollow tubular body 11'. When the UV high pressure mercury lamps are enabled, the ultraviolet light emitting from the lamps includes UVC radiation, which has a central frequency of 250 nm and includes a wavelength range of 200-280 nm, according to the spectrum. Those skilled in the art understand that more than one UV light source with different wavelengths can also be employed to perform sterilization and disinfection for different pathogens without affecting the essence of the present invention. As shown, the UV isolation layer 13' is provided with a first intermediary section 131' and a second intermediary section 133' respectively adjacent to the inlet port 111' and the outlet port 113', to prevent the ultraviolet light from spreading beyond the inlet and outlet ports. In this embodiment, the first and second intermediary sections 131', 133' can be made of a resin added with a UV absorber and can be detachably fixed to the inner surface 117'.

When the UV light source 15' is enabled, since there are no objects able to obstruct the ultraviolet light emitting from the source, the water passing through the UV tube 1' can be uniformly irradiated and disinfected by the ultraviolet light. Since the UV isolation layer 13' has a good ultraviolet reflection effect, under the same power consumption condition, more ultraviolet light can be used on sterilization and disinfection. Furthermore, the first and second intermediary sections 131', 133' can absorb the ultraviolet light spreading out of the UV isolation layer 13' to prevent other areas from being irradiated, thus avoiding damages, such as photodegradation occurring on the hollow tubular body 11' made of plastic.

In the embodiment where the hollow tubular body 11' is sheltered by the UV isolation layer 13', since the UV light source 15' is located at a center of the hollow tubular body 11', the ultraviolet light emitting from the UV light source 15' can be uniformly distributed in the space defined by the inner surface 117', and has an intensity level more than 40 micro-watt/square-centimeter to cause pathogens damages which are difficult to be fixed. In this embodiment, the hollow tubular body 11' has a length about 12 cm. Provided that the tap water flow has a speed about 2 cm/sec, the water flow will take 6 seconds to pass through the hollow tubular body 11'. This uniformly distributed ultraviolet light can achieve a disinfection effect on more than 90% of pathogen species.

Furthermore, an activated carbon filter (not shown) can be provided before the UV tube 1' so as to remove the ordor molecules contained in the water to be treated. Combination of the activated carbon filter and the UV light source further improves the quality of the water. For improving the safety of the UV tube 1', an automatic power-off device can be provided so that, when the UV tube 1' is subjected to an impact or external force, the electrical supply can be cut off, and thus accidental leakage of ultraviolet light can be avoided.

Figure 7:
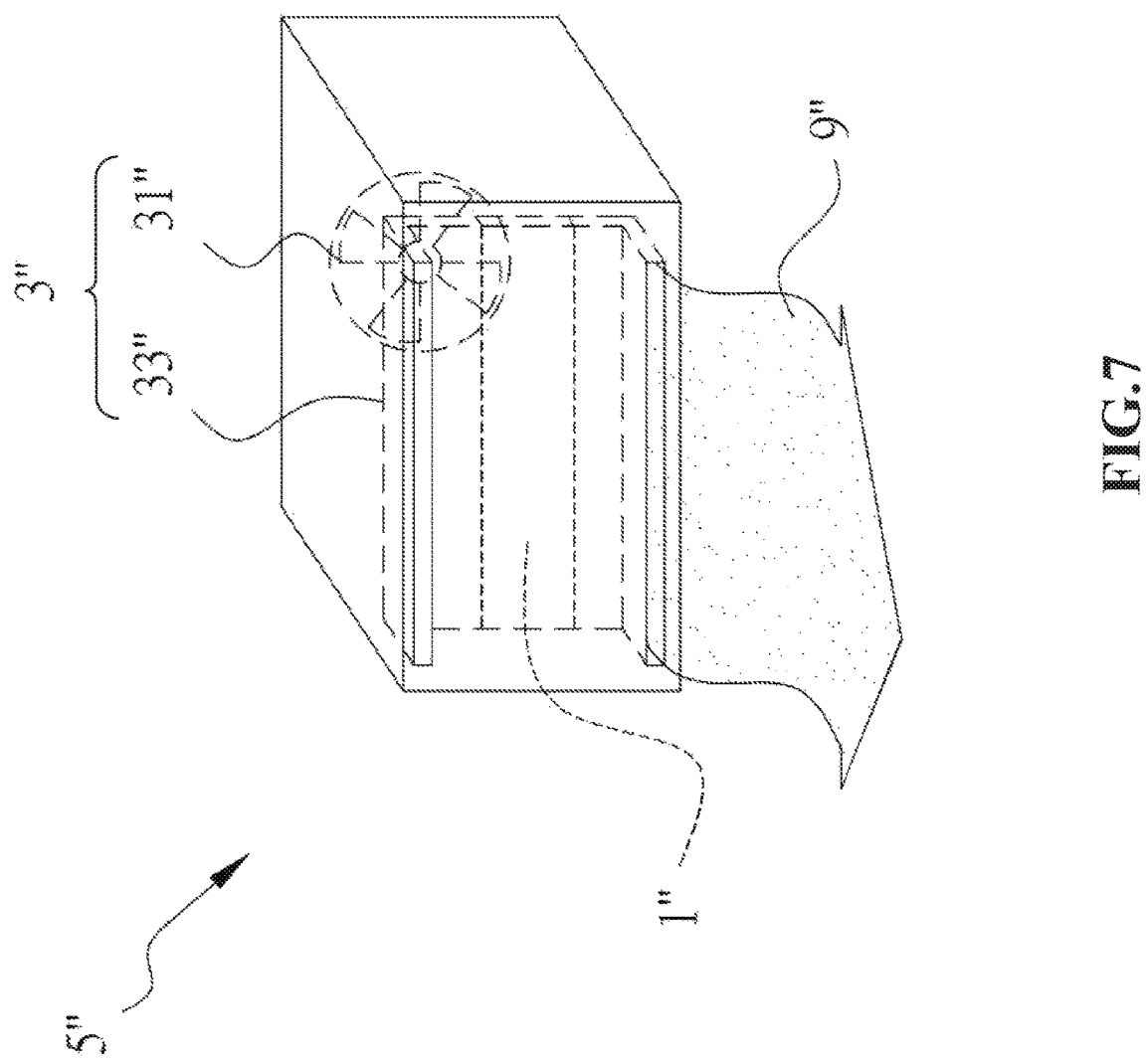
FIG. 7 shows a 3-dimensional schematic view of a third embodiment of the present invention, which shows an internal structure of an air conditioning system.

FIG. 7 shows a third embodiment of the present invention, which is concerned with a household air conditioning system 5" provided with a UV tube 1". Of course, the air conditioning system of the present invention can also been applied to a vehicle or other areas without affecting the essence of the present invention. Since the UV tube 1" of this embodiment is same as that used in the previous embodiments, illustration therefor is omitted herein. As shown, the air conditioning system 5" includes a heat exchange device 33". As an example, the heat exchange device 33" can be a compressor assembly. However, those skilled in the art understand that other types of mechanical assembly, such as a water-cooled cold/heat exchange assembly, can also be employed without affecting the essence of the present invention. In this embodiment, the air fan works as a fluid drive means 31", and the air flow is indicated as a fluid 9".

The heat exchange device 33" and the fluid drive means 31" can work together to form an air heat exchange unit 3". The UV tube 1" can be connected to the air heat exchange unit 3". As an example, the UV tube 1" can replace the heat exchange device 33" such that the processes of heat exchange and sterilization can be conducted at the same time. Of course, the UV tube 1" can be arranged upstream or downstream of the heat exchange device 33" without affecting the essence of the present invention.

While the invention has been described with reference to the preferred embodiments above, it should be recognized that the preferred embodiments are given for the purpose of illustration only and are not intended to limit the scope of the present invention and that various modifications and changes, which will be apparent to those skilled in the relevant art, may be made without departing from the scope of the invention.

What is claimed is:

1. An UV tube for killing microorganisms contained in a fluid delivered by a fluid drive means in connection therewith, the UV tube comprising:

a hollow tubular body having an inlet port, an outlet port, and a fluid channel portion between the inlet port and the outlet port, wherein the inlet port takes in the fluid delivered by the fluid drive means while the outlet port allows the fluid to flow out of the hollow tubular body, and the fluid channel portion has an inner surface;

an UV isolation layer disposed at the inner surface of the hollow tubular body for sheltering the inner surface of the hollow tubular body, the fluid being allowed to flow through the UV isolation layer, the UV isolation layer having a first intermediary section adjacent to the inlet port of the hollow tubular body, and a second intermediary section adjacent to the outlet port of the hollow tubular body;

at least one UV light source provided at the hollow tubular body and/or the UV isolation layer, the UV light source emits ultraviolet light which has a wave length between 100 and 280 nm and reaches a light intensity level more than 40 micro-watt/square-centimeter in at least one portion of a space defined by the inner surface;

wherein the UV isolation layer absorbs and/or reflects at least 80% of the ultraviolet light emitting from the UV light source, so that the possibility of the fluid channel portion being irradiated by the UV light is reduced; and wherein the ultraviolet light emitting from the UV light source is restricted from entering the hollow tubular body by the first and second intermediary sections.

2. The UV tube of claim 1, wherein the fluid channel portion has a predetermined length, so that the fluid delivered by the fluid drive means is exposed to the ultraviolet light for at least 6 seconds when passing through the fluid channel portion.

3. The UV tube of claim 1, wherein the UV light source has a predetermined level of light intensity so that the fluid delivered by the fluid drive means is exposed to the ultraviolet light to at least reach a cumulative light intensity level of 22000 micro-watt sec/square-centimeter.

4. The UV tube of claim 2, further comprising at least one biosensor and at least one processor, the biosensor capable of converting a biological signal to a feedback signal sent back to the processor for determining a light intensity level for the ultraviolet light emitting from the UV light source.

5. The UV tube of claim 1, wherein the UV isolation layer is a ductile metal layer.

6. The UV tube of claim 1, wherein the UV isolation layer is an electroplated metal layer.

7. An air conditioning system, comprising:
at least one air heat exchange unit for receiving an air flow, including:
at least one fluid drive means for receiving the air flow; and
at least one heat exchange device; and
at least one UV tube connected with the air heat exchange unit, the at least one UV tube including:
a hollow tubular body having an inlet port, an outlet port, and a fluid channel portion between the inlet port and the outlet port, wherein the inlet port takes in the air flow delivered by the at least one fluid drive means while the outlet port allows the air to flow out of the hollow tubular body, and the fluid channel portion has an inner surface;
an UV isolation layer disposed at the inner surface of the hollow tubular body for sheltering the inner surface of the hollow tubular body, the air flow being allowed to flow through the UV isolation layer, the UV isolation layer having a first intermediary section adjacent to the inlet port of the hollow tubular body, and a second intermediary section adjacent to the outlet port of the hollow tubular body; and
at least one UV light source provided at the hollow tubular body and/or the UV isolation layer, the UV light source emits ultraviolet light which has a wave length between 100 and 280 nm and reaches a light intensity level more than 40 micro-watt/square-centimeter in at least one portion of a space defined by the inner surface;
wherein the UV isolation layer absorbs and/or reflects at least 80% of the ultraviolet light emitting from the UV light source, so that the possibility of the fluid channel portion being irradiated by the UV light is reduced; and
wherein the ultraviolet light emitting from the UV light source is restricted from entering the hollow tubular body by the first and second intermediary sections.

8. The air conditioning system of claim 7, wherein the fluid channel portion has a predetermined length, and the UV light source has a predetermined light intensity level, so that the air flow delivered by the at least one fluid drive means is exposed to the ultraviolet light for at least 6 seconds when passing through the fluid channel portion, thus reaching a cumulative light intensity level of 22000 micro-watt sec/square-centimeter.

* * * * *